(12) United States Patent
Voss et al.

(10) Patent No.: US 8,980,916 B2
(45) Date of Patent: Mar. 17, 2015

(54) FACTOR IXA INHIBITORS

(71) Applicants: Matthew Voss, The Galen (SG); Hiroki Sone, The Galen (SG); Samuel Chackalamannil, Califon, NJ (US); Munetaka Ohkouchi, Cotemba (JP)

(72) Inventors: Matthew Voss, The Galen (SG); Hiroki Sone, The Galen (SG); Samuel Chackalamannil, Califon, NJ (US); Munetaka Ohkouchi, Cotemba (JP)

(73) Assignees: Merck Sharp & Dohme Corp., Rahway, NJ (US); Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/353,359

(22) PCT Filed: Oct. 24, 2012

(86) PCT No.: PCT/US2012/061625
§ 371 (c)(1),
(2) Date: Apr. 22, 2014

(87) PCT Pub. No.: WO2013/063068
PCT Pub. Date: May 2, 2013

(65) Prior Publication Data
US 2014/0322195 A1 Oct. 30, 2014

Related U.S. Application Data

(60) Provisional application No. 61/551,977, filed on Oct. 27, 2011.

(51) Int. Cl.
| | | |
|---|---|---|
| *A61K 45/06* | (2006.01) | |
| *A61K 31/5377* | (2006.01) | |
| *A61K 31/4725* | (2006.01) | |
| *A61K 31/4439* | (2006.01) | |
| *A61K 31/4375* | (2006.01) | |
| *C07D 471/04* | (2006.01) | |
| *C07D 413/12* | (2006.01) | |
| *C07D 413/14* | (2006.01) | |
| *C07D 401/12* | (2006.01) | |

(52) U.S. Cl.
CPC ............ *C07D 401/12* (2013.01); *C07D 413/14* (2013.01); *C07D 413/12* (2013.01); *C07D 471/04* (2013.01); *A61K 31/4375* (2013.01); *A61K 31/4439* (2013.01); *A61K 31/4725* (2013.01); *A61K 31/5377* (2013.01); *A61K 45/06* (2013.01)
USPC ........ 514/310; 514/314; 514/338; 514/233.8; 546/256; 546/261; 546/143; 546/272.1

(58) Field of Classification Search
USPC ............... 546/256, 261, 143, 272.1; 514/310, 514/338, 233.8, 314
See application file for complete search history.

(56) References Cited

FOREIGN PATENT DOCUMENTS

| | | |
|---|---|---|
| WO | WO0179262 A1 | 10/2001 |
| WO | WO2010065717 A1 | 6/2010 |
| WO | WO2011017296 A1 | 2/2011 |
| WO | WO2011025565 A1 | 3/2011 |
| WO | WO2013009527 A2 | 1/2013 |

OTHER PUBLICATIONS

Is Weller et al., Journal of the American Chemical Society (1976), 98(21), 6650-7.*
International Search Report and Written Opinion of PCT/US 12/61625 mailed Jan. 23, 2013, 8 pages.
Wang et al, Structure Based Drug Design: Development of Potent and Selective Factor IXa (FIXa) Inhibitors, J Med Chem, 2010, 1473-1482, 53.

* cited by examiner

*Primary Examiner* — Niloofar Rahmani
(74) *Attorney, Agent, or Firm* — Nicole M. Beeler; Catherine D. Fitch

(57) ABSTRACT

The present invention provides a compound of Formula (I)

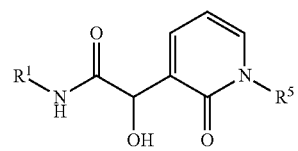

as described herein, or a pharmaceutically acceptable salt thereof. The present invention also provides pharmaceutical compositions comprising one or more said compounds, and methods for using said compounds for treating or preventing a thromboses, embolisms, hypercoagulability or fibrotic changes.

16 Claims, No Drawings

FACTOR IXA INHIBITORS

CROSS REFERENCE TO RELATED APPLICATIONS

This application is a U.S. National Phase application under 35 U.S.C. §371 of PCT Application No. PCT/US12/061625 filed Oct. 24, 2012, which claims priority from U.S. Provisional Application Ser. No. 61/551,977, filed Oct. 27, 2011.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijaykumar et al., *Biorganic & Medicinal Chemistry Letters* (2006), 16 (10), 2796-2799, discloses hydroxy pyrazole based factor IXa inhibitors.

SUMMARY OF THE INVENTION

In its many embodiments, the present invention provides a novel class of compounds, pharmaceutical compositions comprising one or more said compounds, and methods for using said compounds, for treating or preventing thrombus formation, embolisms, hypercoagulability or fibrotic changes.

The compounds of Formula (I) according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound of Formula (I)

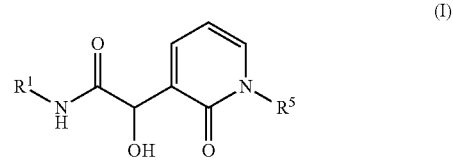

wherein
$R^1$ is
1) an aryl ring, or
2) a heteroaryl ring, wherein the point of attachment to the heteroaryl ring is a carbon atom, and the heteroaryl ring is selected from the group consisting of:
  a) a 5- or 6-membered unsaturated monocyclic ring with 1, 2, 3, or 4 heteroatom ring atoms selected from the group consisting of N, O or S,
  b) an 9- or 10-membered unsaturated bicyclic ring with 1, 2, 3, or 4 heteroatom ring atoms selected from the group consisting of N, O or S,
said aryl and heteroaryl ring is unsubstituted, or independently mono-, di-, or tri-substituted with $R^7$;
$R^5$ is
1) an aryl ring, or
2) a heteroaryl ring, wherein the point of attachment to the heteroaryl ring is a carbon atom, and the heteroaryl ring is selected from the group consisting of:
  a) a 5- or 6-membered unsaturated monocyclic ring with 1, 2, 3, or 4 heteroatom ring atoms selected from the group consisting of N, O or S,
  b) an 9- or 10-membered unsaturated bicyclic ring with 1, 2, 3, or 4 heteroatom ring atoms selected from the group consisting of N, O or S,
said aryl and heteroaryl ring is unsubstituted, or independently mono-, di-, or tri-substituted with $R^9$;
$R^7$, each time in which it occurs, is independently —C(=NR$^{11}$)N(R$^{11}$)$_2$, —N(R$^{11}$)$_2$, —CN or —C$_{1-6}$alkyl;
$R^9$, each time in which it occurs, is independently —OCF$_3$, halogen, —C(O)R$^{10}$, —C$_{1-6}$ alkyl, —N(R$^{12}$)$_2$, —CF$_3$, R$^{10}$ or OR$^{10}$;
$R^{10}$ is a 6-membered heterocycle ring containing 1 or 2 heteroatoms independently selected from O and N, which is unsubstituted or substituted with =O
$R^{11}$ each time in which it occurs, is independently hydrogen or —C$_{1-6}$ alkyl; and
$R^{12}$, each time in which it occurs, is independently hydrogen or —C$_{1-6}$ alkyl,
or a pharmaceutically acceptable salt thereof.

In one embodiment of the invention, $R^7$ is —$NH_2$.

In another embodiment, $R^9$, each time in which it occurs, is independently —$OCF_3$, F, —$C(O)R^{10}$, —$C(CH_3)_3$, $R^{10}$ or $OR^{10}$.

In another embodiment, $R^1$ is a 9- or 10-membered unsaturated bicyclic heteroaryl ring with 1, 2, 3, or 4 heteroatom ring atoms selected from the group consisting of N, O or S, wherein said heteroaryl ring is unsubstituted, or independently mono-, di-, or tri-substituted with $R^9$.

In group of this embodiment, $R^1$ is

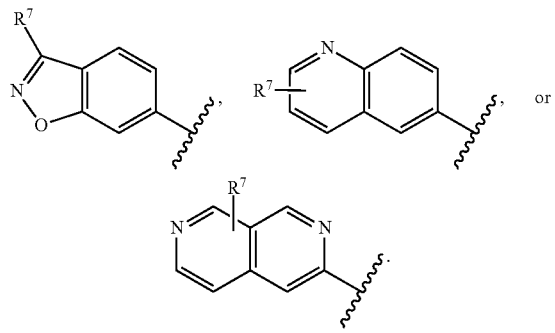

In a family of this group, $R^1$ is

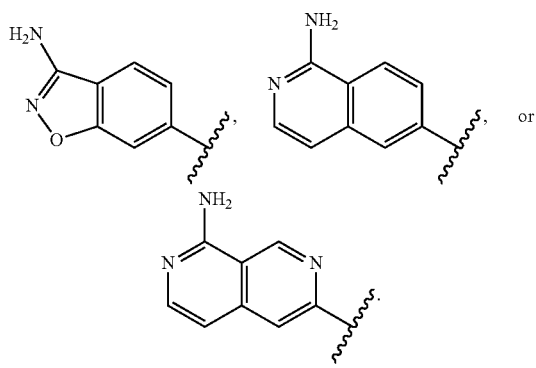

In another embodiment, wherein $R^5$ is aryl, wherein said phenyl ring is unsubstituted, or independently mono-, di-, or tri-substituted with $R^9$.

In a preferred group of this embodiment, $R^5$ is phenyl, wherein said phenyl ring is unsubstituted, or independently mono-, di-, or tri-substituted with $R^9$.

In a family of this group, $R^5$ is

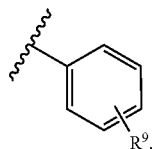

In a subfamily of this family, $R^5$ is

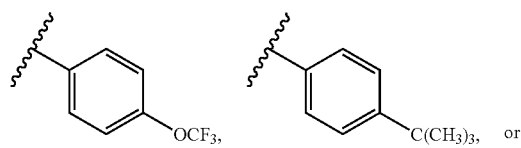

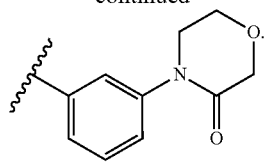

In a second family of this group, $R^5$ is

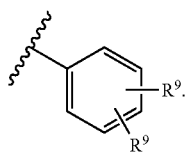

In a subfamily of this second family, $R^5$ is

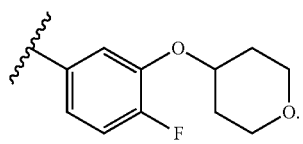 [SMILES: *c1ccc(F)c(OC2CCOCC2)c1]

In another embodiment, $R^9$ is —$OCF_3$, —$C(CH_3)_3$,

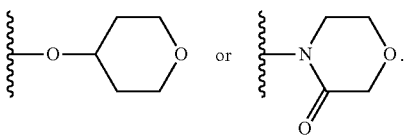 [SMILES: *OC1CCOCC1 ; *N1CCOCC1=O]

In another embodiment, the compound is

N-(3-aminobenzo[d]isoxazol-6-yl)-2-(1-(4-fluoro-3-(tetrahydro-2H-pyran-4-yloxy)phenyl)-2-oxo-1,2-dihydropyridin-3-yl)-2-hydroxyacetamide (Example 1)

(±)-N-(3-aminobenzo[d]isoxazol-6-yl)-2-hydroxy-2-(2-oxo-1-(4-(trifluoromethoxy)phenyl)-1,2-dihydropyridin-3-yl)acetamide (Example 2)

(±)-N-(3-aminobenzo[d]isoxazol-6-yl)-2-hydroxy-2-(2-oxo-1-(3-(3-oxomorpholino)phenyl)-1,2-dihydropyridin-3-yl)acetamide (Example 3).

N-(8-amino-2,7-naphthyridin-3-yl)-2-hydroxy-2-(2-oxo-1-(4-(trifluoromethoxy)phenyl)-1,2-dihydropyridin-3-yl) acetamide (Example 4)

(±)-N-(3-aminobenzo[c/]isoxazol-6-yl)-2-(1-(4-tert-butylphenyl)-2-oxo-1,2-dihydropyridin-3-yl)-2-hydroxyacetamide (Example 5)

(±)-N-(1-aminoisoquinolin-6-yl)-2-(1-(4-tert-butylphenyl)-2-oxo-1,2-dihydropyridin-3-yl)-2-hydroxyacetamide (Example 6)

Pharmaceutically acceptable salts include non-toxic salts such as those derived from inorganic acids, e.g. hydrochloric, hydrobromic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. "$\xi$—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $(C_1$-$C_6$ alkyl)$S(O)_{0-2}$—, $HS(O)_{0-2}$—, $(C_1$-$C_6$ alkyl)$S(O)_{0-2}(C_1$-$C_6$ alkyl)-, $HS(O)_{0-2}(C_1$-$C_6$ alkyl)-, $(C_0$-$C_6$ alkyl)$C(O)NH$—, $H_2N$—$C(NH)$—, —$O(C_1$-$C_6$ alkyl)$CF_3$, $HC(O)$—, $(C_1$-$C_6$ alkyl)$C(O)$—, $HOC(O)$—, $(C_1$-$C_6$ alkyl)$OC(O)$—, $HO(C_1$-$C_6$ alkyl)-, $(C_1$-$C_6$ alkyl)$O(C_1$-$C_6$ alkyl)-, $(C_1$-$C_6$ alkyl)$C(O)_{1-2}(C_1$-$C_6$ alkyl)-, $HC(O)_{1-2}(C_1$-$C_6$ alkyl)-, $(C_1$-$C_6$ alkyl)$C(O)_{1-2}$—, $HOC(O)NH$—, $(C_1$-$C_6$ alkyl)$OC(O)NH$—, aryl, aralkyl, heterocycle, heterocyclylalkyl, haloaryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, the term "aryl", alone or in combination, relates to a phenyl, naphthyl or indanyl group, preferably a phenyl group. The abbreviation "Ph" represents phenyl.

Except where noted herein, the term "heteroaryl" refers to a monocyclic unsaturated ring having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The terms "heterocycle" and "heterocyclic" refer to a saturated monocyclic 5- to 8-membered ring having 1-4 heteroatoms selected from N, O and S, or a 7- to 12-membered saturated or partially saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, aryl groups may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)CF$_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

Except where noted herein, heteroaryl and heterocyclic rings may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)CF$_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NHC$_1$-$C_6$ alkyl, —C(O)NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

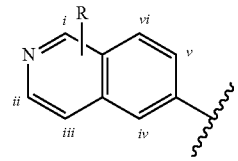

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments which contain an efficacious amount of at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the Formula (I) can be employed in patients who are suffering from disorders of well-being or diseases which accompany thromboses, embolisms, hypercoagulability or fibrotic changes.

These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the Formula (I) can be employed in all interventions which lead to contact of the blood with foreign surfaces, as in dialysis patients and patients with indwelling catheters. Compounds of the Formula (I) can also be employed in order to reduce the risk of thrombosis after surgical interventions such as in knee and hip joint operations.

Compounds of the Formula (I) are suitable for the treatment of patients with disseminated intravascular coagulation, sepsis and other intravascular events which accompany inflammation. Furthermore, compounds of the Formula (I) are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the Formula (I) are suitable for the retardation or prevention of such processes.

Further indications for the use of the compounds of the Formula (I) are fibrotic changes of the lungs such as chronic obstructive pulmonary disease, adult respiratory distress syndrome (ARDS) and of the eye, such as fibrin deposits after eye operations. Compounds of the Formula (I) are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the Formula (I) according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to Formula (I), daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the Formula (I) can be administered both as a monotherapy and in combination with antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The effectiveness of compounds of the present invention to inhibit the coagulation factors XIa, VIIa, IXa, Xa, plasma kallikrein or thrombin, can be determined using a relevant purified serine protease, respectively, and an appropriate synthetic substrate.

Abbreviations: DMSO (dimethylsulfoxide), Et$_3$N (triethylamine), TFA (trifluoroacetic acid), Ac (acetic acid), PMB (p-methoxybenzyl), Pht (phthaloyl).

GENERAL SYNTHESIS

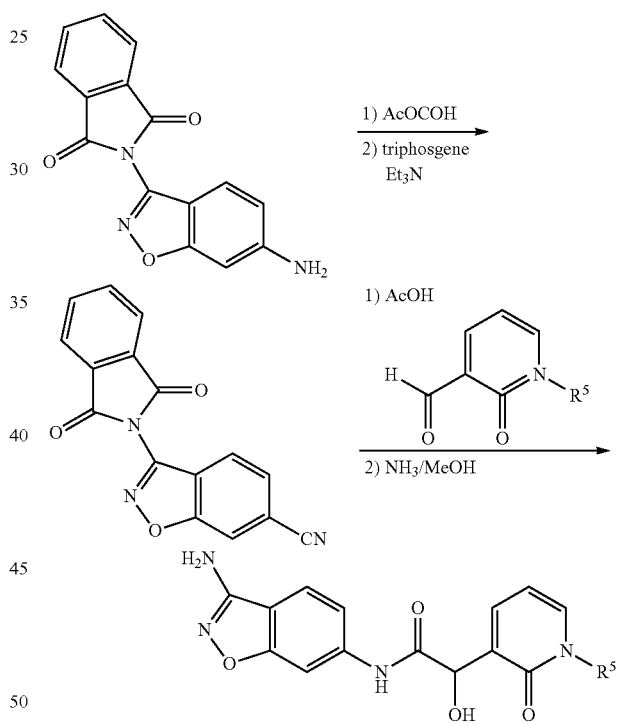

R$^5$ is defined above.

Example 1

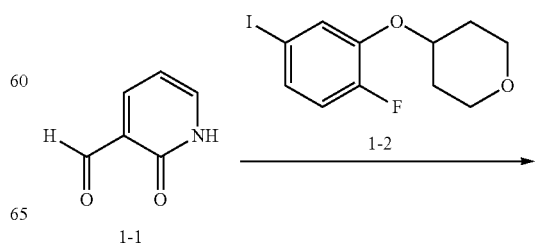

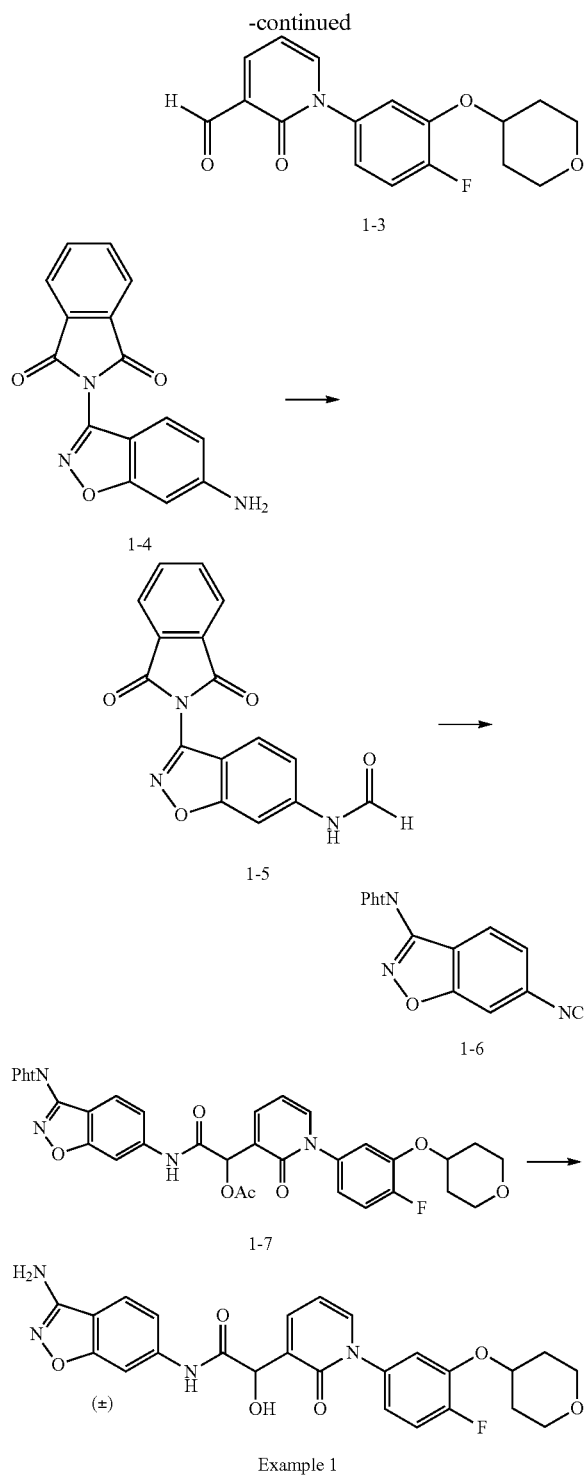

Example 1

Synthesis of 1-(4-fluoro-3-(tetrahydro-2H-pyran-4-yloxy)phenyl)-2-oxo-1,2-dihydropyridine-3-carbaldehyde (1-3)

1-1 (200 mg, 1.63 mmol), 1-2 (628 mg, 1.95 mmol), N,N-dimethylethane-1,2-diamine (57.3 mg, 0.650 mmol), copper iodide (61.9 mg, 0.325 mmol), and potassium phosphate (689 mg, 3.24 mmol) were combined in a round bottom flask with 1,4-dioxane (5.0 mL) under a nitrogen atmosphere and heated to 110° C. for 48 h. The reaction was cooled to room temperature and dilute with water. The mixture was extracted 3 times with ethyl acetate and the combined organic extracts were washed with brine, dried over $Na_2SO_4$, and concentrated in vacuo. Purification by flash column chromatography on silica gel (0-50% EtOAc in $CH_2Cl_2$) gave 104 mg (20%) of 1-3 as an off-white solid: $^1$H NMR (300 MHz, $CDCl_3$) δ 10.33 (1H, s), 8.12 (1H, dd, J=7.2, 2.4 Hz), 7.63 (1H, dd, J=7.2, 2.4 Hz), 7.23-7.19 (1H, m), 7.08 (1H, dd, J=7.2, 2.7 Hz), 6.91 (1H, m), 6.41 (1H, t, J=7.2 Hz), 4.51 (1H, m), 4.03-3.96 (2H, m), 3.60-3.53 (2H, m), 2.09-2.00 (2H, m), 1.91-1.80 (2H, m); ESI-MS m/z 318 $[C_{17}H_{16}FNO_4+H]^+$.

Synthesis of N-(3-(1,3-dioxoisoindolin-2-yl)benzo[d]isoxazol-6-yl)formamide (1-5)

Acetic anhydride (2.63 mL, 27.9 mmol) was added to formic acid (1.04 mL, 27.9 mmol) at 0° C. The mixture was heated to 60° C. for 30 minutes. After that 2-(6-aminobenzo[d]isoxazol-3-yl)isoindoline-1,3-dione 1-4 (390 mg, 1.39 mmol) dissolved in $CH_2Cl_2$ (10 mL) was added at 0° C. The mixture was stirred for 1 h at room temperature. The mixture was concentrated and the residue was triturated with $CH_2Cl_2$/hexane (1:1) to give 300 mg (70%) of 1-5 as a pale yellow solid: $^1$H NMR (300 MHz, DMSO-$d_6$) (rotamer ratio: s-cis/s-trans=3:1) δ 10.75 (0.75H, br s), 10.58 (0.25H, br d, J=11.3 Hz), 9.04 (0.25H, br d, J=11.3 Hz), 8.43 (0.75H, br s), 8.29 (0.75H, br s), 8.07 (2H, m), 7.99 (2H, m), 7.81 (1H, d, J=8.4 Hz), 7.80 (0.25H, br s), 7.43 (0.75H, d, J=8.4 Hz), 7.28 (0.25H, br d, J=8.4 Hz); ESI-MS m/z 308 $[C_{16}H_9N_3O_4+H]^+$.

Synthesis of 2-(6-isocyanobenzo[d]isoxazol-3-yl)isoindoline-1,3-dione (1-6)

1-5 (150 mg, 0.480 mmol) was suspended in $CH_2Cl_2$ (10 mL) and cooled to 0° C. To the mixture were added triphosgene (87.0 mg, 0.290 mmol) followed by $Et_3N$ (0.140 mL, 0.980 mmol). The mixture was stirred at room temperature for 2 h. The mixture was diluted with $CH_2Cl_2$, washed with saturated aqueous $NaHCO_3$, brine and dried over $Na_2SO_4$. The residue was triturated with hexane to give 115 mg (82%) of 1-6 as a pale yellow solid: $^1$H NMR (400 MHz, DMSO-$d_6$) δ 8.34 (1H, br s), 8.09 (2H, m), 8.04 (1H, dd, J=8.4, 0.8 Hz), 8.00 (2H, m), 7.68 (1H, dd, J=8.4, 1.6 Hz); ESI-MS m/z 290 $[C_{16}H_7N_3O_3]^+$.

Synthesis of 2-(3-(1,3-dioxoisoindolin-2-yl)benzo[d]isoxazol-6-ylamino)-1-(1-(4-fluoro-3-(tetrahydro-2H-pyran-4-yloxy)phenyl)-2-oxo-1,2-dihydropyridin-3-yl)-2-oxoethyl acetate (1-7)

To a solution of 1-3 (68.0 mg, 0.214 mmol) in methylene chloride (0.40 mL) were added 1-6 (62.0 mg, 0.214 mmol) followed by acetic acid (0.012 mL, 0.214 mmol), and the reaction mixture was heated to 50° C. for 24 h. After the reaction was completed, solvent was removed in vacuo. The residue was purified by silica gel chromatography (0-50% acetone in hexane) to give 68.0 mg (48%) of 1-7 as an off-white solid: $^1$H NMR (300 MHz, $CDCl_3$) δ 10.01 (1H, s), 8.24 (1H, br s), 8.03 (2H, m), 7.88 (1H, s), 7.86 (2H, m), 7.51 (1H, d, J=8.7 Hz), 7.41 (1H, dd, J=6.9, 1.8 Hz), 7.21 (2H, m), 7.02 (1H, dd, J=7.2, 2.4 Hz), 6.94-6.89 (1H, m), 6.48 (1H, t, J=7.2 Hz), 6.36 (1H, s), 4.51 (1H, m), 4.03-3.96 (2H, m), 3.60-3.53 (2H, m), 2.33 (3H, s), 2.09-2.00 (2H, m), 1.91-1.80 (2H, m); ESI-MS m/z 667 $[C_{35}H_{27}FN_4O_9+H]^+$.

Synthesis of N-(3-aminobenzo[d]isoxazol-6-yl)-2-(1-(4-fluoro-3-(tetrahydro-2H-pyran-4-yloxy)phenyl)-2-oxo-1,2-dihydropyridin-3-yl)-2-hydroxyacetamide

Example 1

A mixture of 1-5 (45.0 mg, 0.0675 mmol) and 7 M $NH_3$ in methanol (5.0 mL, 35.0 mmol) was stirred at room temperature for 1 h. The volatiles were removed under reduced pressure and the residue was purified by silica gel chromatography (0-50% acetone in hexane) followed by trituration with $CH_2Cl_2/Et_2O$ to provide 17.0 mg (52%) of Example 1 as a yellow solid: $^1H$ NMR (400 MHz, $CDCl_3$) δ 10.54 (1H, s), 7.93 (1H, br s), 7.87 (1H, br d, J=7.2 Hz), 7.40-7.37 (2H, m), 7.29-7.22 (1H, m), 7.20 (1H, dd, J=7.7, 1.6 Hz), 7.03 (1H, dd, J=7.2, 2.4 Hz), 6.95-6.91 (1H, m), 6.50 (1H, t, J=6.8 Hz), 5.42 (1H, d, J=4.0 Hz), 4.75 (1H, d, J=4.0 Hz), 4.51 (1H, m), 4.31 (2H, br s), 4.03-3.98 (2H, m), 3.60-3.54 (2H, m), 2.10-2.03 (2H, m), 1.91-1.80 (2H, m); ESI-MS m/z 495 $[C_{25}H_{23}FN_4O_6+H]^+$.

Example 2

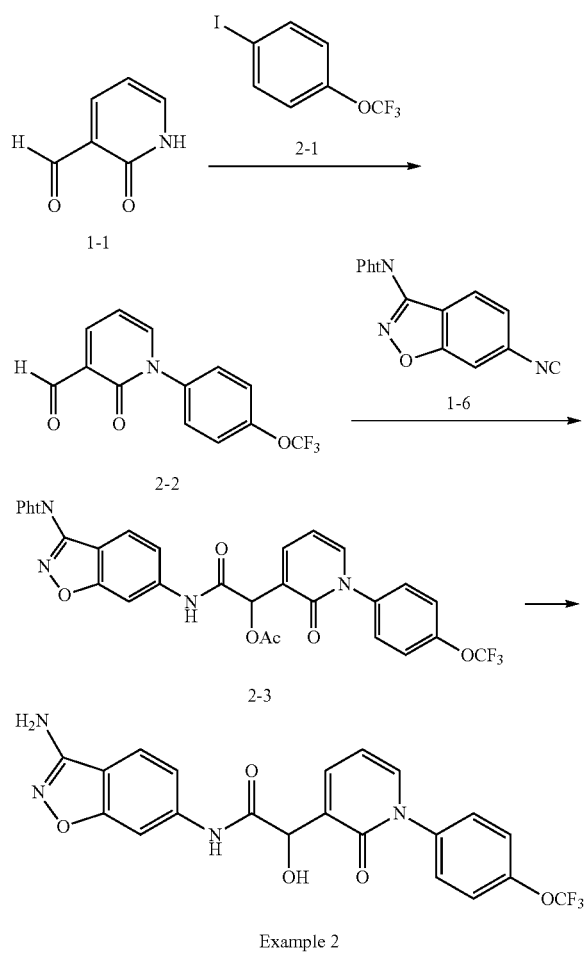

Synthesis of 2-oxo-1-(4-(trifluoromethoxy)phenyl)-1,2-dihydropyridine-3-carbaldehyde (2-2)

2-oxo-1,2-dihydropyridine-3-carbaldehyde 1-1 (200 mg, 1.63 mmol), 1-iodo-4-(trifluoromethoxy)benzene 2-1 (562 mg, 1.95 mmol), 8-hydroxyquinoline (47.2 mg, 0.324 mmol), copper iodide (61.9 mg, 0.324 mmol), and potassium carbonate (303 mg, 2.19 mmol) were combined in a round bottom flask with DMSO (3.5 mL) under a nitrogen atmosphere and heated to 130° C. for 21 h. The reaction was cooled to room temperature and poured into a mixture of 10% aq. ammonium hydroxide and ethyl acetate. The resultant mixture was filtered through a pad of Celite and washed with ethyl acetate three times. The layers were separated with the aqueous portion being back extracted with ethyl acetate. The combined organic extracts were washed with brine, dried over $Na_2SO_4$, and concentrated in vacuo. Purification by flash column chromatography on silica gel (0-50% EtOAc in hexane) gave 92.0 mg (20%) of 2-2 as an off-white solid: $^1H$ NMR (400 MHz, $CDCl_3$) δ 10.34 (1H, d, J=0.8 Hz), 8.14 (1H, dd, J=6.9, 2.3 Hz), 7.65 (1H, dd, J=6.9, 2.3 Hz), 7.45 (2H, m), 7.38 (2H, m), 6.44 (1H, dt, J=0.8, 6.9 Hz); ESI-MS m/z 284 $[C_{13}H_8F_3NO_3+H]^+$.

Synthesis of (±)-2-(3-(1,3-dioxoisoindolin-2-yl)benzo[d]isoxazol-6-ylamino)-2-oxo-1-(2-oxo-1-(4-(trifluoromethoxy)phenyl)-1,2-dihydropyridin-3-yl) ethyl acetate (2-3)

To a solution of 1-6 (325 mg, 1.12 mmol) in methylene chloride (1.9 mL) were added compound 2-2 (212 mg, 0.749 mmol) followed by acetic acid (0.06 mL, 1.12 mmol), and the reaction mixture was heated to 50° C. for 48 h. Then the solvent was removed in vacuo, and the residue was purified by silica gel chromatography (0-50% acetone in hexane) to give 105 mg (22%) of 2-3: $^1H$ NMR (300 MHz, $CDCl_3$) δ 9.94 (1H, s), 8.25 (1H, d, J=1.5 Hz), 8.03 (2H, m), 7.85-7.89 (3H, m), 7.54 (1H, d, J=8.5 Hz), 7.38-7.46 (5H, m), 7.22 (1H, dd, J=8.5, 1.5 Hz), 6.53 (1H, t, J=7.2 Hz), 6.36 (1H, s), 2.33 (3H, s); ESI-MS m/z 633 $[C_{31}H_{19}F_3N_4O_8+H]^+$.

Synthesis of (±)-N-(3-aminobenzo[d]isoxazol-6-yl)-2-hydroxy-2-(2-oxo-1-(4-(trifluoromethoxy)phenyl)-1,2-dihydropyridin-3-yl)acetamide

Example 2

A mixture of 2-3 (105 mg, 0.169 mmol) and 7 M $NH_3$ in methanol (5.0 mL) was stirred at room temperature for 1.75 h. The volatiles were removed under reduced pressure and the residue was purified by silica gel chromatography (0-50% acetone in hexane) followed by trituration with $CH_2Cl_2/Et_2O$ to provide 48.0 mg (51%) of Example 2 as a white solid: $^1H$ NMR (400 MHz, DMSO-$d_6$) δ 10.26 (1H, s), 7.94 (1H, d, J=1.6 Hz), 7.66-7.72 (3H, m), 7.57 (2H, m), 7.51 (2H, m), 7.39 (1H, dd, J=8.4, 1.6 Hz), 6.46 (1H, t, J=6.8 Hz), 6.29 (2H, br s), 6.26 (1H, d, J=6.2 Hz), 5.23 (1H, d, J=6.2 Hz); ESI-MS m/z 461 $[C_{21}H_{15}F_3N_4O_5+H]^+$.

Example 3

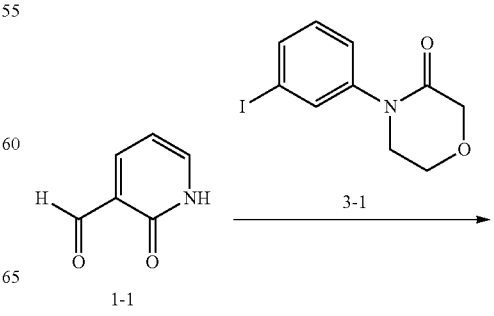

15

-continued

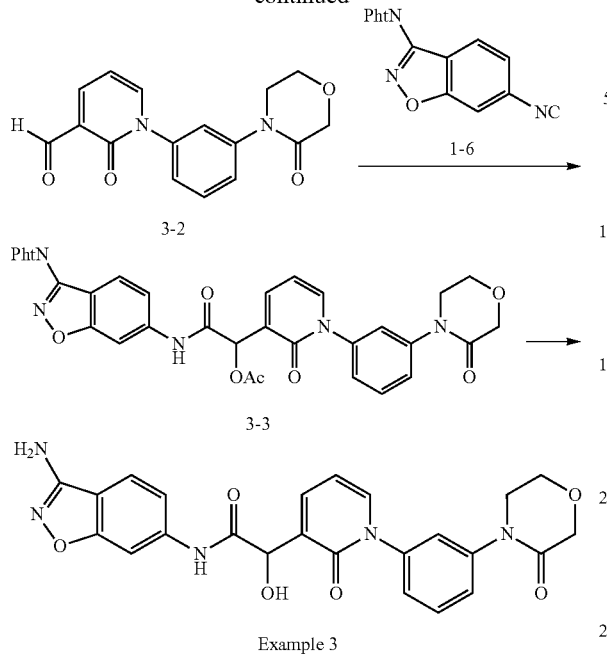

Synthesis of 2-oxo-1-(3-(3-oxomorpholino)phenyl)-1,2-dihydropyridine-3-carbaldehyde (3-2)

30 mL microwave reaction vessel was flushed with nitrogen gas and charged with 2-oxo-1,2-dihydropyridine-3-carbaldehyde 1-1 (100 mg, 0.812 mmol), 4-(3-iodophenyl)morpholin-3-one 3-1 (296 mg, 0.974 mmol), 8-hydroxyquinoline (48.0 mg, 0.324 mmol), copper iodide (31.0 mg, 0.162 mmol), potassium carbonate (152 mg, 1.09 mmol) and DMSO (1.7 mL) under a nitrogen atmosphere. The resulting mixture was irradiated in a microwave apparatus (Biotage) at 150° C. for 15 minutes. The reaction was cooled to room temperature and poured into a mixture of 10% aq. ammonium hydroxide and ethyl acetate. The resultant mixture was filtered through a pad of Celite and washed with ethyl acetate three times. The layers were separated with the aqueous portion being back extracted with ethyl acetate. The combined organic extracts were washed with brine, dried over Na$_2$SO$_4$, and concentrated in vacuo. Purification by silica gel column chromatography (0-100% EtOAc in hexane) gave 61.0 mg (24%) of 3-2 as a light brown solid: $^1$H NMR (400 MHz, CDCl$_3$) δ 10.33 (1H, d, J=0.4 Hz), 8.14 (1H, dd, J=6.8, 2.3 Hz), 7.27 (1H, dd, J=6.8, 2.3 Hz), 7.60 (1H, t, J=8.1 Hz), 7.53 (1H, t, J=2.1 Hz), 7.47 (1H, ddd, J=8.1, 2.1, 1.2 Hz), 7.32 (1H, ddd, J=8.1, 2.1, 1.2 Hz), 6.43 (1H, dt, J=6.8, 0.4 Hz), 4.34 (2H, br, s), 4.03-4.06 (2H, m), 3.84-3.86 (2H, m); ESI-MS m/z 299 [C$_{16}$H$_{14}$N$_2$O$_4$+H]$^+$.

(±)-2-(3-(1,3-dioxoisoindolin-2-yl)benzo[d]isoxazol-6-ylamino)-2-oxo-1-(2-oxo-1-(3-(3-oxomorpholino)phenyl)-1,2-dihydropyridin-3-yl)ethyl acetate 3-3 was synthesized using a procedure similar to the synthesis of compound 2-3: $^1$H NMR (300 MHz, CDCl$_3$) δ 10.03 (1H, s), 8.18 (1H, d, J=1.5 Hz), 8.03 (2H, m), 7.85-7.88 (3H, m), 7.61 (1H, t, J=8.1 Hz), 7.45-7.54 (4H, m), 7.23-7.33 (2H, m), 6.53 (1H, t, J=7.2 Hz), 6.37 (1H, s), 4.35 (2H, s), 4.04-4.09 (2H, m), 3.82-3.89 (2H, m), 2.33 (3H, s); ESI-MS m/z 648 [C$_{34}$H$_{25}$N$_5$O$_9$+H]$^+$.

16

Synthesis of (±)-N-(3-aminobenzo[d]isoxazol-6-yl)-2-hydroxy-2-(2-oxo-1-(3-(3-oxomorpholino)phenyl)-1,2-dihydropyridin-3-yl)acetamide

Example 3

Example 3 was synthesized using a procedure similar to the synthesis of Example 2. Additionally, purification by silica gel chromatography (0-5% MeOH in CH$_2$Cl$_2$) gave Example 3 as a pale green solid: $^1$H NMR (400 MHz, CDCl$_3$) δ 10.55 (1H, s), 7.85-7.9 (2H, m), 7.62 (1H, t, J=8.0 Hz), 7.44-7.53 (3H, m), 7.40 (1H, br d, J=8.4 Hz), 7.32 (1H, m), 7.28 (1H, dd, J=8.4, 1.6 Hz), 6.52 (1H, t, J=6.8 Hz), 5.44 (1H, d, J=5.0 Hz), 4.75 (1H, d, J=5.0 Hz), 4.35 (2H, s), 4.29 (2H, br s), 4.03-4.09 (2H, m), 3.81-3.93 (2H, m); ESI-MS m/z 476 [C$_{24}$H$_{21}$N$_5$O$_6$+H]$^+$.

Example 4

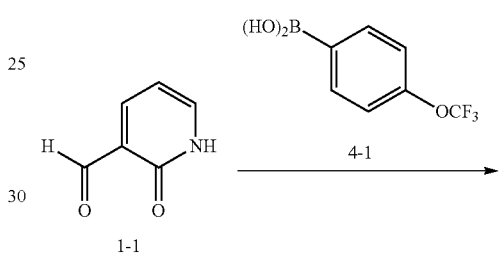

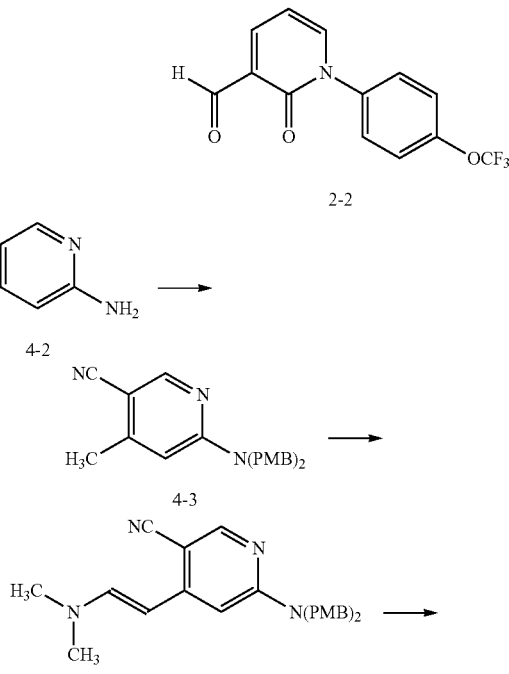

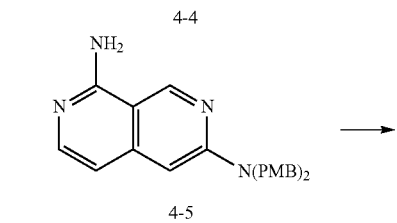

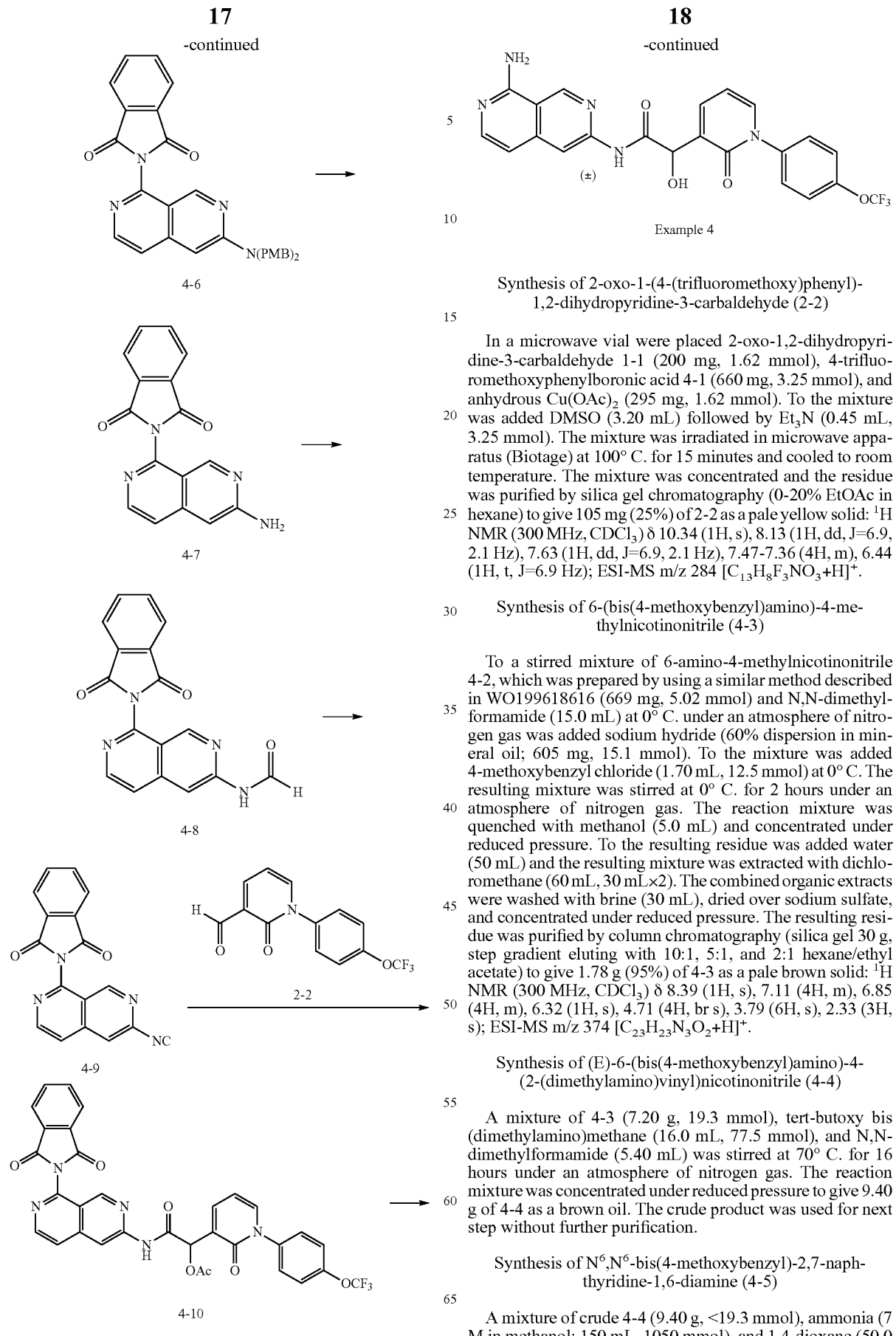

Example 4

Synthesis of 2-oxo-1-(4-(trifluoromethoxy)phenyl)-1,2-dihydropyridine-3-carbaldehyde (2-2)

In a microwave vial were placed 2-oxo-1,2-dihydropyridine-3-carbaldehyde 1-1 (200 mg, 1.62 mmol), 4-trifluoromethoxyphenylboronic acid 4-1 (660 mg, 3.25 mmol), and anhydrous Cu(OAc)$_2$ (295 mg, 1.62 mmol). To the mixture was added DMSO (3.20 mL) followed by Et$_3$N (0.45 mL, 3.25 mmol). The mixture was irradiated in microwave apparatus (Biotage) at 100° C. for 15 minutes and cooled to room temperature. The mixture was concentrated and the residue was purified by silica gel chromatography (0-20% EtOAc in hexane) to give 105 mg (25%) of 2-2 as a pale yellow solid: $^1$H NMR (300 MHz, CDCl$_3$) δ 10.34 (1H, s), 8.13 (1H, dd, J=6.9, 2.1 Hz), 7.63 (1H, dd, J=6.9, 2.1 Hz), 7.47-7.36 (4H, m), 6.44 (1H, t, J=6.9 Hz); ESI-MS m/z 284 [C$_{13}$H$_8$F$_3$NO$_3$+H]$^+$.

Synthesis of 6-(bis(4-methoxybenzyl)amino)-4-methylnicotinonitrile (4-3)

To a stirred mixture of 6-amino-4-methylnicotinonitrile 4-2, which was prepared by using a similar method described in WO199618616 (669 mg, 5.02 mmol) and N,N-dimethylformamide (15.0 mL) at 0° C. under an atmosphere of nitrogen gas was added sodium hydride (60% dispersion in mineral oil; 605 mg, 15.1 mmol). To the mixture was added 4-methoxybenzyl chloride (1.70 mL, 12.5 mmol) at 0° C. The resulting mixture was stirred at 0° C. for 2 hours under an atmosphere of nitrogen gas. The reaction mixture was quenched with methanol (5.0 mL) and concentrated under reduced pressure. To the resulting residue was added water (50 mL) and the resulting mixture was extracted with dichloromethane (60 mL, 30 mL×2). The combined organic extracts were washed with brine (30 mL), dried over sodium sulfate, and concentrated under reduced pressure. The resulting residue was purified by column chromatography (silica gel 30 g, step gradient eluting with 10:1, 5:1, and 2:1 hexane/ethyl acetate) to give 1.78 g (95%) of 4-3 as a pale brown solid: $^1$H NMR (300 MHz, CDCl$_3$) δ 8.39 (1H, s), 7.11 (4H, m), 6.85 (4H, m), 6.32 (1H, s), 4.71 (4H, br s), 3.79 (6H, s), 2.33 (3H, s); ESI-MS m/z 374 [C$_{23}$H$_{23}$N$_3$O$_2$+H]$^+$.

Synthesis of (E)-6-(bis(4-methoxybenzyl)amino)-4-(2-(dimethylamino)vinyl)nicotinonitrile (4-4)

A mixture of 4-3 (7.20 g, 19.3 mmol), tert-butoxy bis(dimethylamino)methane (16.0 mL, 77.5 mmol), and N,N-dimethylformamide (5.40 mL) was stirred at 70° C. for 16 hours under an atmosphere of nitrogen gas. The reaction mixture was concentrated under reduced pressure to give 9.40 g of 4-4 as a brown oil. The crude product was used for next step without further purification.

Synthesis of N$^6$,N$^6$-bis(4-methoxybenzyl)-2,7-naphthyridine-1,6-diamine (4-5)

A mixture of crude 4-4 (9.40 g, <19.3 mmol), ammonia (7 M in methanol; 150 mL, 1050 mmol), and 1,4-dioxane (50.0 mL) was placed in a 350 mL sealed tube. The resulting mixture was stirred at 90° C. for 138 hours and cooled to ambient temperature. The reaction mixture was concentrated under reduced pressure to give 10.9 g of 4-5 as a brown oil. The crude product was used for next step without further purification.

Synthesis of 2-(6-(bis(4-methoxybenzyl)amino)-2,7-naphthyridin-1-yl)isoindoline-1,3-dione (4-6)

To a stirred mixture of crude 4-5 (10.9 g, <19.3 mmol), triethylamine (8.05 mL, 57.8 mmol), and dichloromethane (75.0 mL) at 0° C. under an atmosphere of nitrogen gas was added phthaloyl dichloride (90%; 3.75 mL, 23.4 mmol). The resulting mixture was stirred at ambient temperature for 15 hours under an atmosphere of nitrogen gas. The reaction mixture was quenched with saturated aqueous $NH_4Cl$ (200 mL) and the resulting mixture was extracted with dichloromethane (1000 mL, 500 mL×2). The combined organic extracts were washed with brine (200 mL), dried over sodium sulfate, and concentrated under reduced pressure. The resulting residue was purified by column chromatography (silica gel 200 g, step gradient eluting with 50:1, 40:1, 30:1, 20:1, 10:1, and 5:1 dichloromethane/ethyl acetate) followed by recrystallization from dichloromethane to give 3.94 g (39% in 3 steps) of 4-6 as yellow crystals: $^1$H NMR (400 MHz, $CDCl_3$) δ 8.94 (1H, br s), 8.33 (1H, d, J=6.0 Hz), 8.02 (2H, m), 7.84 (2H, m), 7.31 (1H, dd, J=6.0, 0.8 Hz), 7.15 (4H, m), 6.85 (4H, m), 6.52 (1H, br s), 4.81 (4H, br s), 3.79 (6H, s); ESI-MS m/z 531 $[C_{32}H_{26}N_4O_4+H]^+$.

Synthesis of 2-(6-amino-2,7-naphthyridin-1-yl)isoindoline-1,3-dione (4-7)

A mixture of 4-6 (3.94 g, 7.43 mmol), trifluoroacetic acid (30.0 mL, 392 mmol), and dichloromethane (30.0 mL) was stirred at 40° C. for 19 hours under an atmosphere of nitrogen gas and concentrated under reduced pressure. To the resulting residue was added saturated aqueous $NaHCO_3$ (300 mL) and hexane/dichloromethane (5:1) (150 mL) at ambient temperature. The resulting mixture was stirred vigorously at ambient temperature for 30 minutes. The precipitated solid was filtered, washed with water (60 mL) and hexane/dichloromethane (5:1) (60 mL), and dried under high vacuum to give 2.08 g (96%) of 4-7 as a pale yellow solid: $^1$H NMR (400 MHz, DMSO-$d_6$) δ 9.04 (1H, br s), 8.28 (1H, d, J=6.0 Hz), 8.05 (2H, m), 7.97 (2H, m), 7.55 (1H, br d, J=6.0 Hz), 6.78 (2H, br s), 6.63 (1H, br s); ESI-MS m/z 291 $[C_{16}H_{10}N_4O_2+H]^+$.

Synthesis of N-(8-(1,3-dioxoisoindolin-2-yl)-2,7-naphthyridin-3-yl) formamide (4-8)

Acetic anhydride (2.01 mL, 20.6 mmol) was added to formic acid (0.75 mL, 20.6 mmol) at 0° C. The mixture was heated to 60° C. for 30 minutes. After that 2-(6-amino-2,7-naphthyridin-1-yl)isoindoline-1,3-dione 4-7 (300 mg, 1.03 mmol) dissolved in $CH_2Cl_2$ (10 mL) was added at 0° C. The mixture was stirred for 1 h at room temperature. The mixture was concentrated and the residue was triturated with $CH_2Cl_2$/hexane (1:1) to give 240 mg (73%) of 4-8 as a pale yellow solid: $^1$H NMR (300 MHz, $CDCl_3$)$^1$H NMR (rotamer ratio: s-cis/s-trans=4:1) δ 9.46 (0.2H, br d, J=10.3 Hz), 9.01 (0.8H, br s), 8.75 (0.2H, br d, J=10.3 Hz), 8.68 (1H, br d, J=5.4 Hz), 8.60 (1H, br s), 8.56 (1H, br s), 8.48 (0.8H, br s), 8.03 (2H, m), 7.86 (2H, m), 7.77 (0.8H, br d, J=5.4 Hz), 7.67 (0.2H, br d, J=5.4 Hz); ESI-MS m/z 319 $[C_{17}H_{10}N_4O_3+H]^+$.

Synthesis of 2-(6-isocyano-2,7-naphthyridin-1-yl)isoindoline-1,3-dione (4-9)

4-8 (90.0 mg, 0.280 mmol) was suspended in $CH_2Cl_2$ (10 mL) and cooled to 0° C. To the mixture were added triphosgene (252 mg, 0.85 mmol) followed by $Et_3N$ (0.240 mL, 1.69 mmol). The mixture was stirred at room temperature for 2 h. The mixture was diluted with $CH_2Cl_2$, washed with saturated aqueous $NaHCO_3$, brine, and dried over $Na_2SO_4$. The residue was purified by silica gel chromatography (0-5% EtOAc in $CH_2Cl_2$) to give 73.3 mg (41%) of 4-9 as a pale white solid: $^1$H NMR (300 MHz, $CDCl_3$) δ 9.18 (1H, br s), 8.86 (1H, d, J=5.7 Hz), 8.06 (2H, m), 7.90 (2H, m), 7.85 (1H, br s), 7.84 (1H, d, J=5.7 Hz); ESI-MS m/z 301 $[C_{17}H_8N_4O_2+H]^+$.

Synthesis of 2-(8-(1,3-dioxoisoindolin-2-yl)-2,7-naphthyridin-3-ylamino)-2-oxo-1-(2-oxo-1-(4-(trifluoromethoxy)phenyl)-1,2-dihydropyridin-3-yl)ethyl acetate (4-10)

4-9 (12.0 mg, 0.0400 mmol) was dissolved in $CH_2Cl_2$ (0.20 mL). To the mixture were added 2-2 (23.0 mg, 0.0812 mmol) and $CH_3CO_2H$ (0.02 mL, 0.3491 mmol) and the mixture was stirred at room temperature for 3 h. The mixture was concentrated and the residue was purified by silica gel chromatography (0-15% EtOAc in $CH_2Cl_2$) to give 3.9 mg (15%) of 4-10 as a pale white solid: $^1$H NMR (300 MHz, $CDCl_3$) δ 10.10 (1H, s), 8.97 (1H, s), 8.62 (1H, d, J=5.8 Hz), 8.55 (1H, s), 8.03 (2H, m), 7.87-7.83 (3H, m), 7.68 (1H, d, J=5.8 Hz), 7.47-7.40 (5H, m), 6.45 (1H, t, J=6.9 Hz), 6.41 (1H, s), 2.32 (3H, s); ESI-MS m/z 644 $[C_{32}H_{20}F_3N_5O_7+H]^+$.

Synthesis of N-(8-amino-2,7-naphthyridin-3-yl)-2-hydroxy-2-(2-oxo-1-(4-(trifluoromethoxy)phenyl)-1,2-dihydropyridin-3-yl)acetamide Example 4

4-10 (7.2 mg, 0.011 mmol) was suspended in 7 M $NH_3$ in methanol (1.0 mL, 7.0 mmol) and the mixture was stirred at room temperature for 2 h. The mixture was concentrated and the residue was purified by silica gel chromatography (0-40% acetone in hexane) to give 2.6 mg (50%) of Example 4 as a pale white solid: $^1$H NMR (400 MHz, $CD_3OD$) δ 9.21 (1H, s), 8.28 (1H, s), 7.83 (1H, d, J=6.2 Hz), 7.82-7.81 (1H, m), 7.65 (1H, dd, J=6.8, 2.0 Hz), 7.57 (2H, m), 7.44 (2H, m), 6.86 (1H, d, J=6.2 Hz), 6.55 (1H, t, J=7.2 Hz), 5.41 (1H, s); ESI-MS m/z 472 $[C_{22}H_{16}F_3N_5O_4+H]^+$.

Example 5

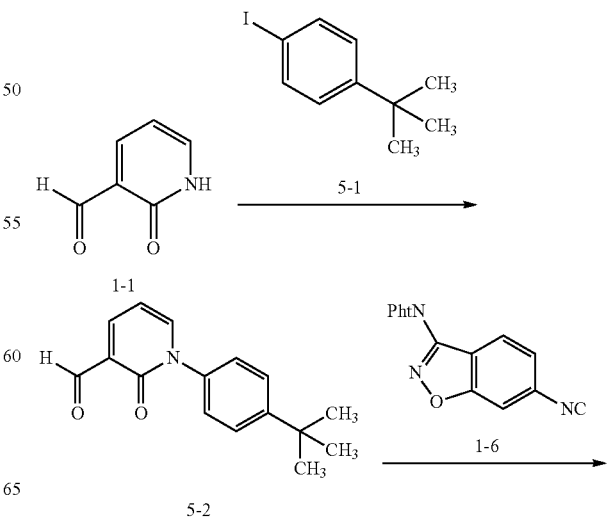

-continued

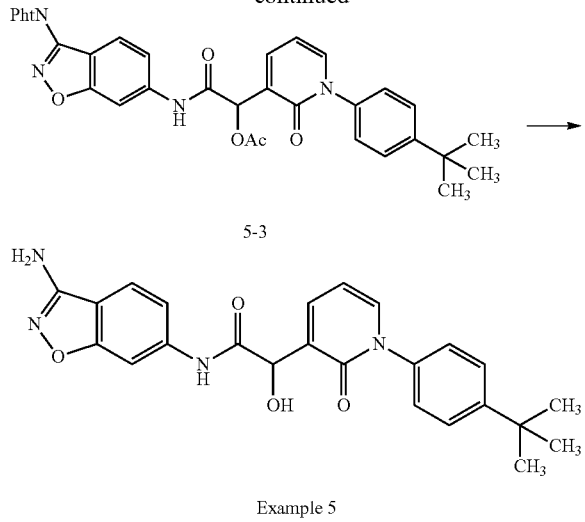

Example 5

1-(4-tert-butylphenyl)-2-oxo-1,2-dihydropyridine-3-carbaldehyde (5-2) was synthesized using a procedure similar to the synthesis of compound 3-2: $^1$H NMR (300 MHz, CDCl$_3$) δ 10.35 (1H, d, J=0.6 Hz), 8.12 (1H, dd, J=6.9, 2.3 Hz), 7.67 (1H, dd, J=6.9, 2.3 Hz), 7.54 (2H, m), 7.32 (2H, m), 6.39 (1H, dt, J=0.6, 6.9 Hz), 1.36 (9H, s); ESI-MS m/z 256 $[C_{16}H_{17}NO_2+H]^+$.

(±)-1-(1-(4-tert-butylphenyl)-2-oxo-1,2-dihydropyridin-3-yl)-2-(3-(1,3-dioxoisoindolin-2-yl)benzo[d]isoxazol-6-ylamino)-2-oxoethyl acetate 5-3 was synthesized using a procedure similar to the synthesis of compound 2-3: $^1$H NMR (400 MHz, CDCl$_3$) δ 10.17 (1H, s), 8.24 (1H, d, J=2.0 Hz), 8.03 (2H, m), 7.83-7.90 (3H, m), 7.51-7.59 (3H, m), 7.45 (1H, dd, J=6.8, 2.0 Hz), 7.30 (2H, m), 7.22-7.27 (2H, m), 6.49 (1H, t, J=6.8 Hz), 2.33 (3H, s), 1.37 (9H, s); ESI-MS m/z 605 $[C_{34}H_{28}N_4O_7+H]^+$.

(±)-N-(3-aminobenzo[d]isoxazol-6-yl)-2-(1-(4-tert-butylphenyl)-2-oxo-1,2-dihydropyridin-3-yl)-2-hydroxyacetamide (Example 5) was synthesized using a procedure similar to the synthesis of Example 3: $^1$H NMR (400 MHz, DMSO-d$_6$) δ 10.26 (1H, s), 7.94 (1H, d, J=1.6 Hz), 7.63-7.71 (3H, m), 7.52 (2H, m), 7.38 (1H, dd, J=8.8, 1.6 Hz), 7.32 (2H, m), 6.41 (1H, t, J=7.2 Hz), 6.29 (2H, br s), 6.24 (1H, br d, J=4.0 Hz), 5.23 (1H, br d, J=4.0 Hz), 1.31 (9H, s); ESI-MS m/z 433 $[C_{24}H_{24}N_4O_4+H]^+$.

Example 6

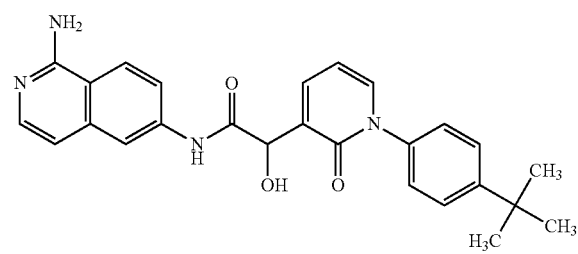

(±)-N-(1-aminoisoquinolin-6-yl)-2-(1-(4-tert-butylphenyl)-2-oxo-1,2-dihydropyridin-3-yl)-2-hydroxyacetamide (Example 6) was synthesized using a procedure similar to Example 5: $^1$H NMR (400 MHz, DMSO-d$_6$) δ 10.21 (1H, s), 8.11 (1H, d, J=9.2 Hz), 8.09 (1H, d, J=2.2 Hz), 7.71 (1H, d, J=6.0 Hz), 7.66 (2H, d, J=6.8 Hz), 7.61 (1H, dd, J=9.2, 2.2 Hz), 7.52 (2H, m), 7.32 (2H, m), 6.78 (1H, d, J=6.0 Hz), 6.72 (2H, br s), 6.42 (1H, t, J=6.8 Hz), 6.23 (1H, d, J=5.8 Hz), 5.25 (1H, d, J=5.8 Hz), 1.30 (9H, s); ESI-MS m/z 442 $[C_{26}H_{26}N_4O_3+H]^+$.

| EXAMPLE | $^1$H NMR (ppm 400 MHz)* |
|---|---|
| 1 | CDCl$_3$ δ 10.54 (1H, s), 7.93 (1H, br s), 7.87 (1H, br d, J = 7.2 Hz), 7.40-7.37 (2H, m), 7.29-7.22 (1H, m), 7.20 (1H, dd, J = 7.7, 1.6 Hz), 7.03 (1H, dd, J = 7.2, 2.4 Hz), 6.95-6.91 (1H, m), 6.50 (1H, t, J = 6.8 Hz), 5.42 (1H, d, J = 4.0 Hz), 4.75 (1H, d, J = 4.0 Hz), 4.51 (1H, m), 4.31 (2H, br s), 4.03-3.98 (2H, m), 3.60-3.54 (2H, m), 2.10-2.03 (2H, m), 1.91-1.80 (2H, m). |
| 2 | DMSO-d$_6$ δ 10.26 (1H, s), 7.94 (1H, d, J = 1.6 Hz), 7.66-7.72 (3H, m), 7.57 (2H, m), 7.51 (2H, m), 7.39 (1H, dd, J = 8.4, 1.6 Hz), 6.46 (1H, t, J = 6.8 Hz), 6.29 (2H, br s), 6.26 (1H, d, J = 6.2 Hz), 5.23 (1H, d, J = 6.2 Hz). |
| 3 | CDCl$_3$ δ 10.55 (1H, s), 7.85-7.9 (2H, m), 7.62 (1H, t, J = 8.0 Hz), 7.44-7.53 (3H, m), 7.40 (1H, br d, J = 8.4 Hz), 7.32 (1H, m), 7.28 (1H, dd, J = 8.4, 1.6 Hz), 6.52 (1H, t, J = 6.8 Hz), 5.44 (1H, d, J = 5.0 Hz), 4.75 (1H, d, J = 5.0 Hz), 4.35 (2H, s), 4.29 (2H, br s), 4.03-4.09 (2H, m), 3.81-3.93 (2H, m). |
| 4 | CD$_3$OD δ 9.21 (1H, s), 8.28 (1H, s), 7.83 (1H, d, J = 6.2 Hz), 7.82-7.81 (1H, m), 7.65 (1H, dd, J = 6.8, 2.0 Hz), 7.57 (2H, m), 7.44 (2H, m), 6.86 (1H, d, J = 6.2 Hz), 6.55 (1H, t, J = 7.2 Hz), 5.41 (1H, s). |
| 5 | DMSO-d$_6$ δ 10.26 (1H, s), 7.94 (1H, d, J = 1.6 Hz), 7.63-7.71 (3H, m), 7.52 (2H, m), 7.38 (1H, dd, J = 8.8, 1.6 Hz), 7.32 (2H, m), 6.41 (1H, t, J = 7.2 Hz), 6.29 (2H, br s), 6.24 (1H, br d, J = 4.0 Hz), 5.23 (1H, br d, J = 4.0 Hz), 1.31 (9H, s). |
| 6 | DMSO-d$_6$ δ 10.21 (1H, s), 8.11 (1H, d, J = 9.2 Hz), 8.09 (1H, d, J = 2.2 Hz), 7.71 (1H, d, J = 6.0 Hz), 7.66 (2H, d, J = 6.8 Hz), 7.61 (1H, dd, J = 9.2, 2.2 Hz), 7.52 (2H, m), 7.32 (2H, m), 6.78 (1H, d, J = 6.0 Hz), 6.72 (2H, br s), 6.42 (1H, t, J = 6.8 Hz), 6.23 (1H, d, J = 5.8 Hz), 5.25 (1H, d, J = 5.8 Hz), 1.30 (9H, s). |

*Except when noted.

| | LC-MS | | | HPLC | |
|---|---|---|---|---|---|
| EXAMPLE | m/z $[M + H]^+$ | RT min | Solvent system | RT min | Solvent system |
| 1 | 495 | 2.02 | A | 21.98 | B |
| 2 | 461 | 2.17 | A | 19.41 | C |
| 3 | 476 | 1.72 | A | 14.85 | C |
| 4 | 472 | 1.66 | A | 24.33 | B |
| 5 | 433 | 2.43 | A | 20.70 | C |
| 6 | 443 | 1.84 | A | 20.98 | B |

Solvent system A: Shim-pack XR-ODS II (2.0×75 mm, 2.2μ); flow: 0.4 mL/min; solvent A: 0.05% HCO$_2$H in H$_2$O; solvent B: 0.05% HCO$_2$H in MeCN; Gradient Table: 0.0 min: 10% B; 0.2 min: 10% B; 0.6 min: 50% B; 2.5 min: 90% B; 3.2 min: 90% B; 3.5 min: 10% B; 5.0 min: 10% B; stop time 5.0 min.
Solvent system B: Luna C18(2) (4.6×250 mm, 5.0μ); flow: 1.0 mL/min; solvent A: 0.05% TFA in H$_2$O; solvent B: 0.05% TFA in MeCN; Gradient Table: 0 min: 10% B; 5 min: 10% B; 20 min: 90% B; 30 min: 90% B; 35 min: 10% B; 40 min: 10% B; stop time 40 min.
Solvent system C: XTerra MS C18 (4.6×150 mm, 5.0μ); flow: 1.0 mL/min; solvent A: 0.05% TFA in H$_2$O; solvent B: 0.05% TFA in MeCN; Gradient Table: 0 min: 10% B; 2.5 min: 10% B; 20 min: 90% B; 30 min: 90% B; 32.5 min: 10% B; 40 min: 10% B; stop time 40 min.
Solvent system D: Alltima C18 column (2.1×100 mm, 3.0μ); flow 0.4 mL/min; solvent A: 0.05% HCO$_2$H in H$_2$O; solvent B: 0.05% HCO$_2$H in MeOH; Gradient Table: 0.0 min: 20% B; 0.30 min 20% B; 2.50 min: 95% B; 4.70 min: 95% B: 4.75 min: 20% B; 6.00 min: 20% B; stop time 6.00 min.

Determination of Inhibitory Activity Against Factor IXa
Inhibitory activity against Factor IXa was tested using the substrate SPECTROFLUOR FIXa (American Diagnostica Inc.; 500 West Avenue, Stamford, Conn. 06902 USA; Pr. No. 299F) and human Factor IXa (American Diagnostica Inc.; Pr. No. 449b). Test substances dissolved in buffer A (50 mM α,α,α-tris(hydroxymethyl)methylamine (Tris), 100 mM NaCl, 5 mM $CaCl_2$, 15% (v/v) ethylene glycol, pH 8.0) were mixed with Factor IXa (2.0 µg/ml final concentration). The enzyme reaction was started by addition of SPECTROFLUOR FIXa (100 µM final concentration). After incubation for 60 minutes at room temperature, the reaction was stopped by the addition of 20% (v/v) acetic acid solution, and then fluorescence value measured (Excitation Wavelength: 355 nm, Emission Wavelength; 460 nm) in a microtiter plate reader (ARVO 1420 Multilabel Counter; PerkinElmer).

$IC_{50}$ was calculated from a dilution series of the test substance with the aid of the software, Symix Assay Explorer (Symyx Technologies, Inc.). Table 3 shows the results.

TABLE 3

| Compound | Factor IXa enzyme assay $IC_{50}$ [nM] |
|---|---|
| 2 | 8600 |
| 5 | 1000 |
| 6 | 54 |

Determination of Inhibitory Activity Against Factor Xa

Inhibitory activity against Factor Xa is tested using the substrate SPECTROFLUOR FXa (American Diagnostica Inc.; 500 West Avenue, Stamford, Conn. 06902 USA; Pr. No. 222F) and human factor Xa (American Diagnostica Inc.; Pr. No. 526). Test substances dissolved in buffer B (20 mM Tris, 200 mM NaCl, 2.5 mM $CaCl_2$, pH 8.0) are mixed with factor Xa (44 ng/ml final concentration). The enzyme reaction is started by addition of SPECTROFLUOR FXa (100 µM final concentration). After incubation for 60 minutes at room temperature, the reaction is stopped by the addition of 20% (v/v) acetic acid solution, and then fluorescence value measured (Excitation Wavelength: 355 nm, Emission Wavelength; 460 nm) in a microtiter plate reader (ARVO 1420 Multilabel Counter; PerkinElmer).

Selectivity Calculation

Selectivity for Factor IXa activity over Factor Xa activity can be determined by the following calculation: (IC50 Factor Xa)/(IC50 Factor IXa). Similar calculations can be made for selectivity of compounds for Factor IXa compared to other coagulation factors. These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Because of their inhibitory action, these compounds are indicated for use in the prevention or treatment of physiological reactions, conditions including thromboembolic disorder (arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis), blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anticoagulant or coagulation inhibitory agents anti-platelet or platelet inhibitory agents, anti-inflammatory agents, thrombin inhibitors, thrombolytic or fibrinolytic agents, thrombin receptor (PAR-1) antagonists, factor VIIa inhibitors, factor VIIIa inhibitor, factor IXa inhibitors different from the compounds of Formula I, factor Xa inhibitors, factor XIa inhibitors, a TAFI inhibitor, and fibrinogen receptor antagonists. Additionally, compounds of the invention can be administered in combination with warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, a ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagnonist, an ET receptor antagonist, a Dual ET/AII antagonist, a neutral endopeptidase inhibitor, a vasopepsidase inhibitor, a Class I agent, a Class II agent, a Class III agent, a Class IV agent, an IAch inhibitor, an IKur inhibitor and a cardiac glycoside.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

One or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of Formula I, and also includes free-acid, free-base and pharmaceutically acceptable salts of said additional active agents when such forms are sold commercially or are otherwise chemically possible. Generally, any suitable additional active agent or agents, including but not limited to antihypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-di-isopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor VIIa inhibitors, VIIIa inhibitors, IXa inhibitors, Xa inhibitors, XIa inhibitors, fibrinogen receptor antagonists (including abciximab, eptifibatide and tirofiban), TAFI inhibitors, and others known in the art. Factor IXa inhibitors different from the compounds of Formula (I) include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulents. *Arterioscler Thromb Vasc Biol.* 2007; 27: 722-727.).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine, prasugrel, clopidogrel, elinogrel, ticagrelor and cangrelor, including pharmaceutically acceptable salts or prodrugs thereof. Clopidogrel is an even more preferred agent. Ticlopidine and clopidogrel are also preferred compounds since they are known to be gentle on the gastrointestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479.

Substituted tricyclic thrombin receptor antagonists are disclosed in U.S. Pat. Nos. 6,063,847, 6,326,380 and WO 01/96330 and Ser. No. 10/271,715.

Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes, as described, for example, in European Patent Application No. 028,489. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); IAch inhibitors, and IKur inhibitors (e.g., compounds such as those disclosed in WO01/40231).

What is claimed is:
1. A compound of Formula (I)

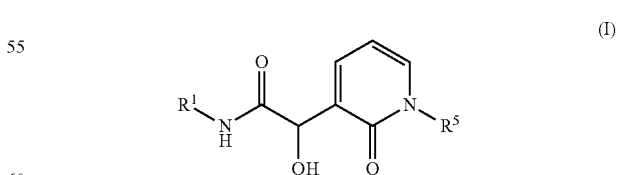

wherein
R$^1$ is
 1) an aryl ring, or
 2) a heteroaryl ring, wherein the point of attachment to the heteroaryl ring is a carbon atom, and the heteroaryl ring is selected from the group consisting of:

a) a 5- or 6-membered unsaturated monocyclic ring with 1, 2, 3, or 4 heteroatom ring atoms selected from the group consisting of N, O or S,
b) an 9- or 10-membered unsaturated bicyclic ring with 1, 2, 3, or 4 heteroatom ring atoms selected from the group consisting of N, O or S, said aryl and heteroaryl ring is unsubstituted, or independently mono-, di-, or tri-substituted with R⁷;

R⁵ is
1) an aryl ring, or
2) a heteroaryl ring, wherein the point of attachment to the heteroaryl ring is a carbon atom, and the heteroaryl ring is selected from the group consisting of:
    a) a 5- or 6-membered unsaturated monocyclic ring with 1, 2, 3, or 4 heteroatom ring atoms selected from the group consisting of N, O or S,
    b) an 9- or 10-membered unsaturated bicyclic ring with 1, 2, 3, or 4 heteroatom ring atoms selected from the group consisting of N, O or S, said aryl and heteroaryl ring is unsubstituted, or independently mono-, di-, or tri-substituted with R⁹;

R⁷, each time in which it occurs, is independently —C(=NR¹¹)N(R¹¹)₂, —N(R¹¹)₂, —CN or —C₁₋₆ alkyl;

R⁹, each time in which it occurs, is independently —OCF₃, halogen, —C(O)R¹⁰, —C₁₋₆ alkyl, —N(R¹²)₂, —CF₃, R¹⁰ or OR¹⁰;

R¹⁰ is a 6-membered heterocycle ring containing 1 or 2 heteroatoms independently selected from O and N, which is unsubstituted or substituted with =O;

R¹¹, each time in which it occurs, is independently hydrogen or —C₁₋₆ alkyl; and R¹², each time in which it occurs, is independently hydrogen or —C₁₋₆ alkyl;

or a pharmaceutically acceptable salt thereof.

2. The compound of claim 1, or a pharmaceutically acceptable salt thereof, wherein R⁷ is —NH₂.

3. The compound of claim 1, or a pharmaceutically acceptable salt thereof, wherein R⁹, each time in which it occurs, is independently —OCF₃, F, —C(O)R¹⁰, —C(CH₃)₃, R¹⁰ or OR¹⁰.

4. The compound of claim 1, or a pharmaceutically acceptable salt thereof, wherein R¹ is a 9- or 10-membered unsaturated bicyclic heteroaryl ring with 1, 2, 3, or 4 heteroatom ring atoms selected from the group consisting of N, O or S, wherein said heteroaryl ring is unsubstituted, or independently mono-, di-, or tri-substituted with R⁹.

5. The compound of claim 4, or a pharmaceutically acceptable salt thereof, wherein R¹ is

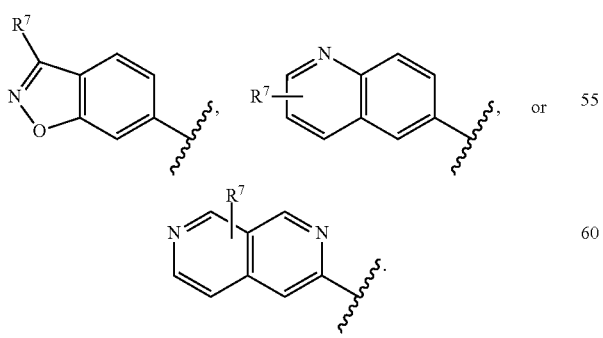

6. The compound of claim 5, or a pharmaceutically acceptable salt thereof, wherein R¹ is

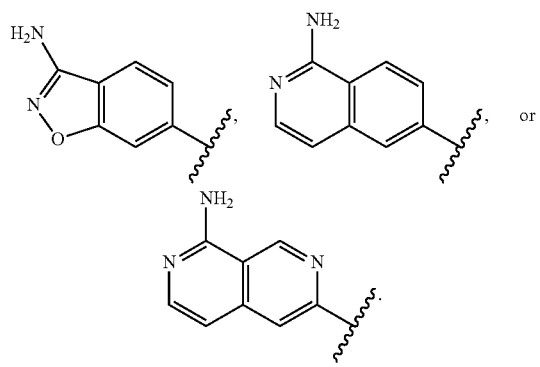

7. The compound of claim 1, or a pharmaceutically acceptable salt thereof, wherein R⁵ is aryl, wherein said phenyl ring is unsubstituted, or independently mono-, di-, or tri-substituted with R⁹.

8. The compound of claim 7, or a pharmaceutically acceptable salt thereof, wherein R⁵ is phenyl, wherein said phenyl ring is unsubstituted, or independently mono-, di-, or tri-substituted with R⁹.

9. The compound of claim 8, or a pharmaceutically acceptable salt thereof, wherein R⁵ is

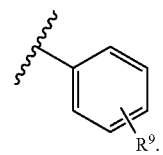

10. The compound of claim 8, or a pharmaceutically acceptable salt thereof, wherein R⁵ is

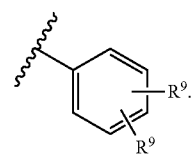

11. The compound of claim 10, or a pharmaceutically acceptable salt thereof, wherein R⁵ is

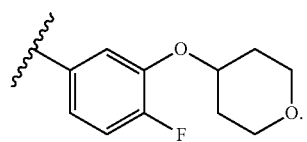 [SMILES: *c1ccc(F)c(OC2CCOCC2)c1]

12. The compound of claim 1, or a pharmaceutically acceptable salt thereof, wherein R⁹ is —OCF₃, —C(CH₃)₃,

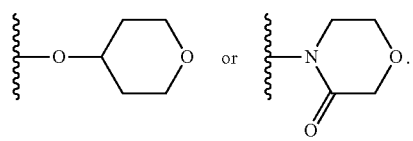

13. A compound of claim 1, or a pharmaceutically acceptable salt thereof, which is N-(3-aminobenzo[d]isoxazol-6-yl)-2-(1-(4-fluoro-3-(tetrahydro-2H-pyran-4-yloxy)phenyl)-2-oxo-1,2-dihydropyridin-3-yl)-2-hydroxyacetamide, (±)-N-(3-aminobenzo[d]isoxazol-6-yl)-2-hydroxy-2-(2-oxo-1-(4-(trifluoromethoxy)phenyl)-1,2-dihydropyridin-3-yl)acetamide, (±)-N-(3-aminobenzo[d]isoxazol-6-yl)-2-hydroxy-2-(2-oxo-1-(3-(3-oxomorpholino)phenyl)-1,2-dihydropyridin-3-yl)acetamide, N-(8-amino-2,7-naphthyridin-3-yl)-2-hydroxy-2-(2-oxo-1-(4-(trifluoromethoxy)phenyl)-1,2-dihydropyridin-3-yl)acetamide, (±)-N-(3-aminobenzo[c/]isoxazol-6-yl)-2-(1-(4-tert-butylphenyl)-2-oxo-1,2-dihydropyridin-3-yl)-2-hydroxyacetamide, or (±)-N-(1-aminoisoquinolin-6-yl)-2-(1-(4-tert-butylphenyl)-2-oxo-1,2-dihydropyridin-3-yl)-2-hydroxyacetamide.

14. A pharmaceutical composition comprising at least one compound of claim 1, or a pharmaceutically acceptable salt thereof, and at least one pharmaceutically acceptable carrier.

15. A pharmaceutical composition comprising a therapeutically effective amount of at least one compound of claim 1 or a pharmaceutically acceptable salt thereof, and at least one pharmaceutically acceptable carrier, and an effective amount of at least one agent selected from the group consisting of anticoagulants, anti-thrombin agents, anti-platelet agents, fibrinolytics, hypolipidemic agents, antihypertensive agents, and anti-ischemic agents.

16. A pharmaceutical composition comprising a therapeutically effective amount of at least one compound of claim 1 or a pharmaceutically acceptable salt thereof, and at least one pharmaceutically acceptable carrier, and an effective amount of at least one agent selected from the group consisting of warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, a ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/AII antagonist, a neutral endopeptidase inhibitor, a vasopepsidase inhibitor, a Class I agent, a Class II agent, a Class III agent, a Class IV agent, an IAch inhibitor, an IKur inhibitor and a cardiac glycoside.

* * * * *